United States Patent [19]
Heinze et al.

[11] Patent Number: 4,830,488
[45] Date of Patent: May 16, 1989

[54] MEASURING INSTRUMENT FOR INTRACARDIAL ACQUISITION OF BLOOD OXYGEN SATURATION

[75] Inventors: Roland Heinze, Munich; Hakan Elmqvist, Baiersdorf, both of Fed. Rep. of Germany

[73] Assignee: Siemens Aktiengesellschaft, Berlin and Munich, Fed. Rep. of Germany

[21] Appl. No.: 51,857

[22] Filed: May 20, 1987

[30] Foreign Application Priority Data

Jun. 16, 1986 [DE] Fed. Rep. of Germany ....... 3620279

[51] Int. Cl.⁴ ...................... G01N 33/48; A61N 1/36; A61N 1/365
[52] U.S. Cl. ................. 356/41; 128/419 PG
[58] Field of Search .................. 356/41; 128/563, 564, 128/419 P, 419 PG

[56] References Cited

U.S. PATENT DOCUMENTS 3,913,403 10/1975 Acara ..................................... 374/173
4,399,820 8/1983 Wirtzfeld et al. ............ 128/419 PG

FOREIGN PATENT DOCUMENTS 3152963 9/1982 Fed. Rep. of Germany .

Primary Examiner—Vincent P. McGraw
Attorney, Agent, or Firm—Hill, Van Santen, Steadman & Simpson

[57] ABSTRACT

A measuring instrument for obtaining an intracardial signal indicative of blood oxygen saturation, which may be used to control the stimulation frequency of a heart pacemaker, has a measuring probe which contains a light transmitter and a light receiver. The light receiver receives light from the light transmitter reflected by the blood. The light transmitter and the light receiver are connected in parallel to an evaluation circuit via two leads. A constant current source is connected in series with the light transmitter. The current generated by the light receiver, indicative of blood oxygen saturation, can be identified by forming the difference between current flowing in the measuring probe and the constant current. A reference measurement to compensate for factors in the total current resulting from the lead resistances and the measuring probe temperature is not necessary.

4 Claims, 2 Drawing Sheets 4,830,488

MEASURING INSTRUMENT FOR INTRACARDIAL ACQUISITION OF BLOOD OXYGEN SATURATION

RELATED APPLICATION

The subject matter of the present application is related to the subject matter of copending application Ser. No. 052,032 (Hans Dieter Liess and Roland Heinze) filed May 19, 1987.

BACKGROUND OF THE INVENTION

1. Field of the Invention

The present invention is directed to a measuring instrument for intracardial acquisition of the blood oxygen saturation which can be used to control the frequency of stimulation pulses supplied to a patient by a heart pacemaker, and in particular to such a measuring instrument having a light emitter and a light receiver, wherein the light receiver receives light from the light transmitter reflected by the blood.

2. Description of the Prior Art

A measuring instrument is disclosed in German OS No. 31 52 963 having a light emitter and a light receiver contained in a measuring probe disposed in a patient's heart. The transmitter and receiver are connected in parallel to an evaluation circuit via two leads. The probe includes a light emitting diode and a phototransistor connected in parallel such that the conducting state current through the light emitting diode is superimposed with the current through the phototransistor caused by the influence of light. If the measuring probe is operated with a constant current or a constant voltage, the light reflected by the blood causes a current change in the phototransistor dependent on the oxygen saturation of the blood, which in turn causes a change in the current or voltage at the measuring probe which is "seen" by the evaluation circuit. The change in voltage or current generated by light reflection is identified by comparing the measured signal to a reference signal.

The reference signal is generated using a pulse, such as a voltage pulse, having the same magnitude but an opposite operational sign, as is used for the useful signal measurement. This pulse is conducted through a diode connected with polarity opposite to that of the light emitting diode. The operating characteristic of the diode in the reference circuit and the characteristics of the light emitting diode are preferably identical.

In this conventional measuring instrument, therefore, only two electrical leads are necessary to make both the useful signal measurement and the reference measurement. This is of particular significance because such lead must be accomodated in a catheter, which preferably has the smallest possible diameter and high flexibility. Moreover, the presence of each additional lead within the catheter increases the possibility of a malfunction.

A disadvantage of this conventional instrument, however, is the necessity of re-polarization of the measured signal, i.e., the necessity of generating a signal for the reference measurement which is of opposite polarity to the signal used for the useful signal measurement. Given the standard format of the voltage supply in heart pacemakers, wherein one pole of the supply voltage is permanently connected to the housing, this repolarization capability involves a significant circuit outlay. Another disadvantage is that the same current is used for the reference measurement as for the useful signal measurement.

SUMMARY OF THE INVENTION

It is an object of the present invention to provide a measuring probe of the type discussed above wherein a reference measurement is not necessary.

The above object is achieved in accordance with the principles of the present invention in a measuring instrument wherein a constant current source is connected in series with the light transmitter. The current $i_S$ flowing in the measuring probe thus consists of a reception current $i_E$, which contains the desired measurable variable, and of a known constant current $i_K$. A separate reference measurement to eliminate the influences of temperature and lead resistance is thus not necessary.

The constant current source, in a further embodiment, may be switchable between different currents. The power of the light transmitter can thus be varied as needed, for example, the power may be increased given intensified attenuation due to deposits.

In one embodiment, the light transmitter may include a red light-emitting diode and an infrared emitting diode, wherein the wavelength of the radiation from the infrared emitting diode is in a range at which reflection thereof by the blood is independent of the blood oxygen saturation. The infrared emitting diode and the light emitting diode are connected in parallel to the light receiver through a switching means in series with the constant current source. This embodiment permits a reference measurement to be made using the infrared emitting diode, however, this reference is not for the same purpose as the reference measurement described above, but rather is for the purpose of eliminating the influences of deposits on the measuring probe instead of the influences of lead resistances and temperature.

DESCRIPTION OF THE PREFERRED EMBODIMENTS

Figure 1:
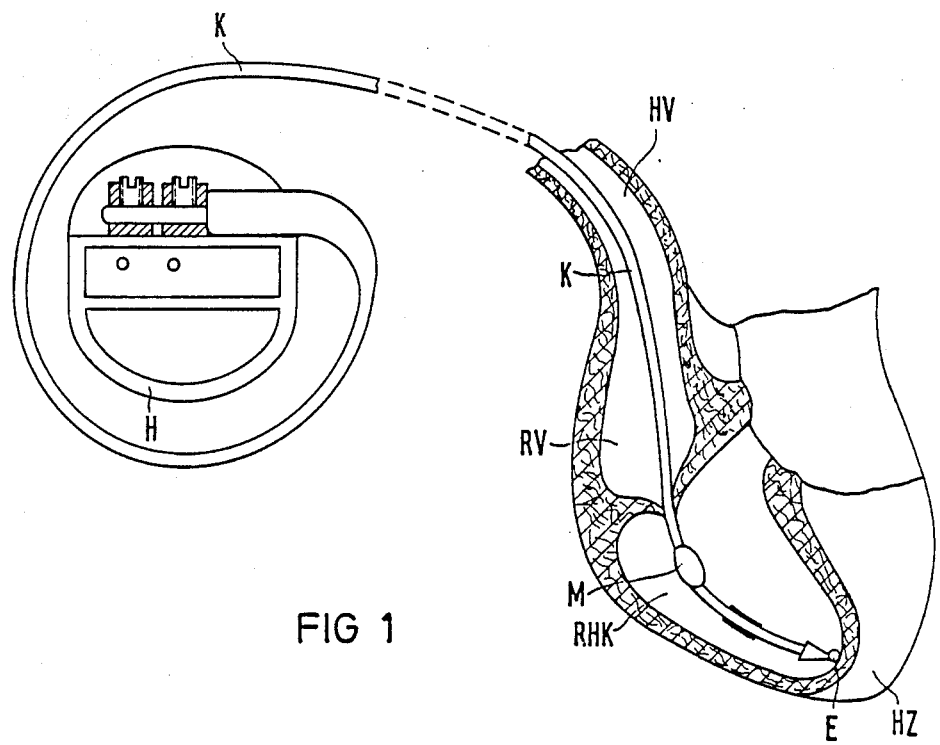
FIG. 1 is a schematic diagram showing a measuring instrument constructed in accordance with the principles of the present invention in the environment of a patient's heart and connected to a heart pacemaker.

A heart pacemaker H is shown in FIG. 1 having a catheter K containing two electrical leads (not shown) which is guided into the superior vena cava HV, through the right atrium RV, and into the right ventricle RHK of a patients heart HZ. A measuring probe M is disposed within the right ventricle RHK, and the catheter K terminates in a stimulation electrode E.

Figure 2:
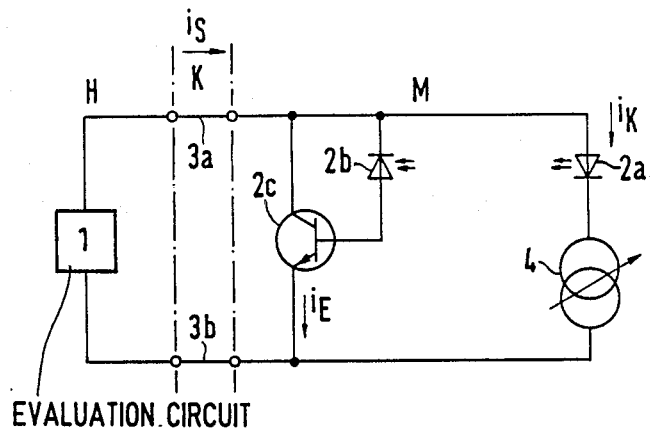
FIG. 2 is a circuit diagram of one embodiment of a measuring instrument constructed in accordance with the principles of the present invention using a constant current source.

A circuit diagram showing details of the measuring probe M in a first embodiment is shown in FIG. 2. The measuring probe M includes the series circuit of a light transmitter, such as a red light-emitting diode 2a, and a constant current source 4. The measuring probe M also includes a light receiver in the form of a phototransistor 2c having a light-sensitive, collector-base diode 2b. The collector-emitter path of the transistor 2c is connected in parallel with the above-described series circuit of the light-emitting diode 2a and the constant current source 4.

The conductivity of the transistor 2c is dependent on the conductivity of the light-sensitive diode 2b. The light-sensitive diode 2b is arranged so as to receive light from the light transmitter 2a reflected by the blood in an amount dependent on the oxygen saturation of the blood. The current $i_E$ flowing through the light receiver thus represents a measure for the oxygen saturation of the blood. The total current $i_S$ flowing in the measuring probe M through the leads 3a and 3b of the catheter K to an evaluation circuit 1 consists of the receiver current $i_E$ and the current flowing through the transmitter 2a. The current through the transmitter 2a is maintained at a constant value $i_K$ by the constant current source 4. The current $i_E$, relevant as the measurable variable, can therefore be identified in a simple manner in the evaluation circuit 1 (which is disposed within the pacemaker H) by subtracting the fixed constant current $i_K$ from the total current $i_S$. In contrast to conventional measuring instruments, therefore, an undefined division of the probe current $i_S$ into the transmission and reception circuits does not occur, instead the current through the reception circuit is fixed. A separate reference measurement for eliminating the influence of the resistance of the leads 3a and 3b and the temperature of the measuring probe M is thus not necessary.

The constant current of the constant current source 4 can be adjustable, indicated by the arrow in FIG. 2. This has the advantage that, for example, the transmission current, and thus the luminous intensity, can be increased when a greater attenuation of the transmission path occurs in the course of time due to deposits on the measuring probe. The change in the constant current $i_K$ is preferably controlled by the evaluation circuit 1, and can be taken into consideration in identifying the measured current.

Figure 3:
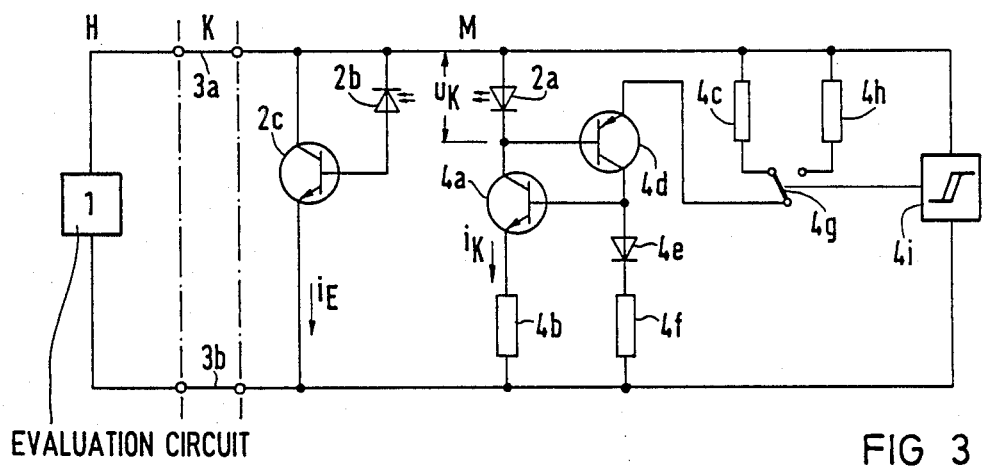
FIG. 3 is a circuit diagram of another embodiment of a measuring instrument constructed in accordance with the principles of the present invention showing details of the constant current source, which is switchable between two current values.

The details of the constant current source 4 of FIG. 2 are shown in detail in the embodiment of FIG. 3. In FIG. 3, reference symbols beginning with the number 4 identify components of the constant current source.

The collector-emitter path of an NPN transistor 4a and a resistor 4b are connected in series with the light transmitter 2a. A series circuit consisting of a resistor 4f, a diode 4e and a PNP transistor 4d is connected between the lines 3a and 3b. This series circuit is directly connected to the line 3b, and is connected to the line 3a through a switching means 4g. Dependent on the position of the switching means 4g, connection to the line 3a is made either through a resistor 4c or a resistor 4h. The switching means 4g is operated by a threshold circuit 4i having an input side connected to the lines 3a and 3b.

The base of the transistor 4a is connected to the junction of the collector of the transistor 4d and the diode 4e. The base of the transistor 4d is connected to the junction of the light transmitter 2a and the collector of the transistor 4a. The current through the transistor 4a, and thus through the light transmitter 2a, is controlled to a constant value $i_K$ because the voltage $u_K$ across the light emitting diode 2a likewise remains constant given a constant current.

When the voltage across the lines 3a and 3b reaches a value which switches the threshold circuit 4i, the resistor 4h is cut into the circuit instead of the resistor 4c, thereby changing the magnitude of the constant current $i_K$.

Figure 4:
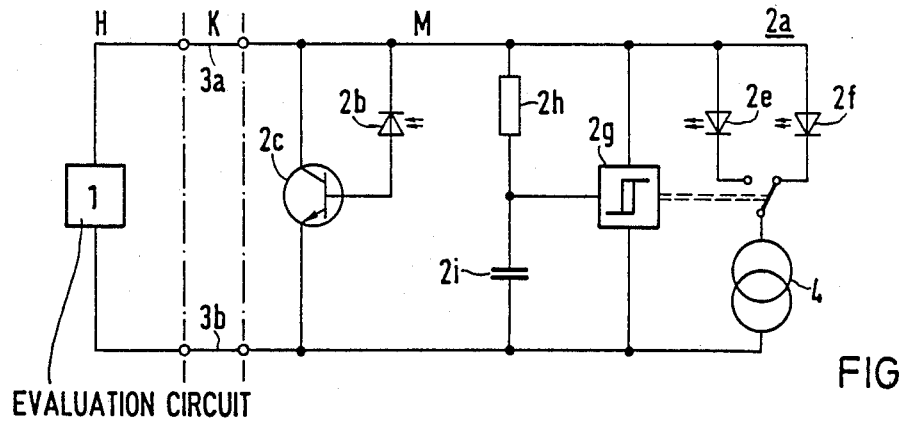
FIG. 4 is a circuit diagram of a further embodiment of a measuring instrument constructed in accordance with the principles of the present invention which permits a reference measurement for compensating for the influence of deposits on the probe to be undertaken.

An embodiment wherein two different light transmitters are provided as shown in FIG. 4. One of the light transmitters is a red light emitting diode 2e for the useful signal measurement, and the other light transmitter is an infrared emitting diode 2f for making a reference measurement to compensate for the influence of deposits on the probe M. The light emitting diode 2e and the infrared emitting diode 2f are selectively connectible to the leads 3a and 3b through a switching means 2d and the constant current source 4. The switching means 2d is controlled by a timing element and a Schmitt trigger 2g. The timing element is in the form of an RC circuit consisting of a resistor 2h and a capacitor 2i connected across the leads 3a and 3b. The input of the Schmitt trigger 2g is connected to the tap of the RC element. A phototransistor 2c having a light-sensitive collector-base diode 2b is, as before connected across the leads 3a and 3b as the light receiver.

When the measuring probe M is charged with current of voltage, the capacitor 2i initially remains uncharged, and the switch 2e is in the position shown in FIG. 4, so that the infrared emitting diode 2f is energized. The infrared emitting diode 2f emits radiation having a wavelength at which the reflection thereof by the blood is independent of the oxygen saturation of the blood, but is dependent on deposits which may be present on the measuring probe. A reference value is thus obtained wherein such deposits are taken into consideration, and which can be employed for correction in the subsequent measurement. The actual measuring procedure is initiated when the voltage across the capacitor 2i exceeds the trigger voltage of the Schmitt trigger 2g, and thus the light emitting diode 2e is energized through the switching means 2d. A signal dependent on the blood oxygen saturation is thus obtained as before.

As in the previous embodiments, the light transmitter in the embodiment of FIG. 4 (consisting of both the light emitting diode 2e and the infrared emitting diode 2f) is connected in series with the constant current source 4 so that the temperature of the measuring probe and the lead resistances need not be separately taken into consideration in an additional reference measurement.

In conventional measuring instruments of this type, a load resistor, which controls the current division between the light transmitter 2a and the light receiver 2b, always connected in series with the light transmitter 2a. In such conventional devices, this load resistor must be relatively large, because only then is an adequate sensitivity of the measuring probe achieved. Such a load resistor is not needed in the measuring instrument disclosed herein due to the connection of a constant current source in series with the light transmitted 2a. The voltage losses associated with the constant current source are significantly less than those associated with a corresponding load resistor, thereby resulting in a further saving of current, in addition to the saving of current due to the elimination of the reference measurement.

Although modifications and changes may be suggested by those skilled in the art it is the intention of the inventors to embody within the patent warranted hereon all changes and modifications as reasonably and properly come within the scope of their contribution to the art.

We claim as our invention:

1. A measuring instrument for intracardial acquisition of the blood oxygen saturation of a patient for use with an evaluation circuit having two leads, said measuring instrument comprising:

means for transmitting light;

means connected across said leads for receiving light from said means for transmitting light reflected by said blood at a level indicative of the oxygen saturation of said blood; and a constant current source connected in series with said means for transmitting light across said leads.

2. A measuring instrument as claimed in claim 1, wherein said constant current source includes means for switching the current thereof between at least two different constant values.

3. A measuring instrument as claimed in claim 1, wherein said means for transmitting light consists of a first light transmitter which transmits radiation having a wavelength which is reflected by the blood dependent on said oxygen saturation thereof and a second light transmitter which emits radiation at a wavelength which is reflected by said blood independently of the oxygen saturation thereof, and wherein said measuring instrument further comprises means for switching between said first and second light transmitters.

4. A measuring instrument as claimed in claim 3, wherein said means for switching between said first and second light transmitters comprises:

a switch connected in series with said constant current source;

a trigger circuit connected to operate said switch and having an input; and an RC element connected across said leads and having a tap connected to said input of said trigger circuit, whereby a capacitor in said RC circuit is charged by said evaluation circuit and said trigger circuit switches said switch when the charge on said capacitor reaches a selected level.

* * * * *